(12) United States Patent
Coffey et al.

(10) Patent No.: US 7,708,987 B2
(45) Date of Patent: *May 4, 2010

(54) METHODS FOR PREVENTING REOVIRUS RECOGNITION FOR THE TREATMENT OF CELLULAR PROLIFERATIVE DISORDERS

(75) Inventors: Matthew C. Coffey, Calgary (CA); Bradley G. Thompson, Calgary (CA)

(73) Assignee: Oncolytics Biotech Inc., Calgary, Alberta (CA)

( * ) Notice: Subject to any disclaimer, the term of this patent is extended or adjusted under 35 U.S.C. 154(b) by 18 days.

This patent is subject to a terminal disclaimer.

(21) Appl. No.: 11/809,195

(22) Filed: May 30, 2007

(65) Prior Publication Data

US 2008/0075729 A1    Mar. 27, 2008

Related U.S. Application Data

(63) Continuation of application No. 11/255,849, filed on Oct. 21, 2005, now Pat. No. 7,452,723, which is a continuation of application No. 10/401,032, filed on Mar. 28, 2003, now Pat. No. 7,014,847, which is a continuation of application No. 09/636,597, filed on Aug. 10, 2000, now Pat. No. 6,565,831, which is a continuation-in-part of application No. 09/256,824, filed on Feb. 24, 1999, now Pat. No. 6,136,307, which is a continuation-in-part of application No. 08/911,383, filed on Aug. 13, 1997, now Pat. No. 6,110,461.

(51) Int. Cl.
*A61K 48/00* (2006.01)
*A61K 39/15* (2006.01)
*A61K 39/42* (2006.01)
*C12N 7/04* (2006.01)

(52) U.S. Cl. ............... 424/93.2; 424/93.1; 424/215.1; 424/1.33; 424/1.61; 435/320.1; 435/235.1; 435/325

(58) Field of Classification Search ........... 424/93.1, 424/93.2; 435/320.1
See application file for complete search history.

(56) References Cited

U.S. PATENT DOCUMENTS

| | | | |
|---|---|---|---|
| 4,108,983 A | 8/1978 | Wallack | |
| 5,023,252 A | 6/1991 | Hseih | |
| 6,136,307 A | 10/2000 | Lee et al. | |
| 6,565,831 B1 | 5/2003 | Coffey et al. | |
| 7,198,783 B2 * | 4/2007 | Morris et al. | 424/93.1 |
| 7,452,723 B2 * | 11/2008 | Coffey et al. | 424/131.1 |

FOREIGN PATENT DOCUMENTS

| | | |
|---|---|---|
| EP | 0 453 242 A1 | 10/1991 |
| EP | 0 514 603 A1 | 11/1992 |
| WO | WO 90/09441 | 8/1990 |
| WO | WO 90/11765 | 10/1990 |
| WO | WO 94/18992 | 9/1994 |
| WO | WO 97/04805 | 2/1997 |
| WO | WO 97/16443 | 5/1997 |
| WO | WO 97/45142 | 12/1997 |
| WO | WO 98/08541 | 3/1998 |
| WO | WO 99/08692 | 2/1999 |
| WO | WO 99/18799 | 4/1999 |
| WO | WO 00/20041 | 4/2000 |
| WO | WO 01/17537 | 3/2001 |

OTHER PUBLICATIONS

Norman et al., "Reovirus as a novel oncolytic agent" *J. Clin. Invest.* 105(8):1035-7 (2000).

Andreansky, S.S., et al. (1996). The application of genetically engineered herpes simplex viruses to the treatment of experimental brain tumors. Proc Natl Acad Sci USA. 93(21):11313-11318.

(Continued)

*Primary Examiner*—Gary B. Nickol
*Assistant Examiner*—Bao Qun Li
(74) *Attorney, Agent, or Firm*—Fish & Richardson P.C.

(57) ABSTRACT

The present invention pertains to methods for preventing reovirus recognition in the treatment of cellular proliferative disorders, and particularly ras-mediated cellular proliferative disorders, in mammals. The mammal may be selected from dogs, cats, sheep, goats, cattle, horses, pigs, mice, humans and non-human primates. The method comprises suppressing or otherwise inhibiting the immune system of the mammal and, concurrently or subsequently, administering to the proliferating cells an effective amount of one or more reoviruses under conditions which result in substantial lysis of the proliferating cells. In particular, the methods provide for reovirus treatment of immunosuppressed or immuno-deficient mammals to treat the proliferative disorders. Immunosuppression, immunoinhibition or otherwise inducing an immunodeficient state in a mammal renders the reovirus more effective. The methods may include the selective removal of immune constituents that may interfere with the systemic delivery of the virus; preventing reovirus recognition by the host immune system; and removal of the virus from an immune suppressed or immune incompetent host following treatment with reovirus. Alternatively, reovirus may be administered to a mammal with a diminished immune response system under conditions which result in substantial lysis of the proliferating cells. Immune systems may be compromised by one or more of the following: an HIV infection; as a side effect of chemotherapy or radiation therapy; by selective removal of B and/or T cell populations; by removal of antibodies (anti-antireovirus antibodies or all antibodies), and the like.

19 Claims, No Drawings

OTHER PUBLICATIONS

Armstrong, G.D., et al. (1984). Studies on reovirus receptors of L cells: virus binding characteristics and comparison with reovirus receptors of erythrocytes. Virology. 138(1):37-48.

Aronheim, A., et al. (1994). Membrane targeting of the nucleotide exchange factor Sos is sufficient for activating the Ras signaling pathway. Cell. 78(6):949-961.

Avruch, J., et al. (1994). Raf meets Ras: completing the framework of a signal transduction pathway. Trends Biochem Sci. 19(7):279-283.

Baldari, C.T., et al. (1992). Interleukin-2 promoter activation in T-cells expressing activated Ha-ras. J Biol Chem. 267(7):4289-4291.

Barbacid, M. (1987). Ras genes. Annu Rev Biochem. 56:779-827.

Berrozpe, G., et al. (1994). Comparative analysis of mutations in the p53 and K-ras genes in pancreatic cancer. Int J Cancer. 58(2):185-191.

Bischoff, J.R., and Samuel, C.E. (1989). Mechanism of interferon action. Activation of the human P1/eIF-2 $\alpha$ protein kinase by individual reovirus s-class mRNAs: s1 mRNA is a potent activator relative to s4 mRNA. Virology. 172(1):106-115.

Bollag, G., et al. (1996). Loss of NF1 results in activation of the Ras signaling pathway and leads to aberrant growth in haematopoietic cells. Nat Genet. 12(2):144-148.

Bos, J.L. (1989). Ras oncogenes in human cancer: a review. Cancer Res. 49(17):4682-4689.

Boviatsis, E.J., et al. (1994). Antitumor activity and reporter gene transfer into rat brain neoplasms inoculated with herpes simplex virus vectors defective in thymidine kinase or ribonucleotide reductase. Gene Ther. 1(5):323-331.

Bryson, J.S., and Cox, D.C. (1988). Characteristics of reovirus-mediated chemoimmunotherapy of murine L1210 leukemia. Cancer Immunol Immunother. 26(2):132-138.

Cahill, M.A., et al. (1996). Signalling pathways: jack of all cascades. Curr Biol. 6(1):16-19.

Coffey, M.C., et al. (1998). Reovirus therapy of tumors with activated Ras pathway. Science. 282(5392):1332-1334.

Chambers, R., et al. (1995). Comparison of genetically engineered herpes simplex viruses for the treatment of brain tumors in a scid mouse model of human malignant glioma. Proc Natl Acad Sci USA. 92(5):1411-1415.

Chandran, K., and Nibert, N. L. (1998). Protease cleavage of reovirus capsid protein µ1/µ1C is blocked by alkyl sulfate detergents, yielding a new type of infectious subvirion particle. J Virol. 72(1):467-475.

Chaubert, P., et al. (1994). K-ras mutations and p53 alterations in neoplastic and nonneoplastic lesions associated with longstanding ulcerative colitis. Am J Pathol. 144(4):767-775.

Cuff, C.F., et al. (1998). Enteric reovirus infection as a probe to study immunotoxicity of the gastrointestinal tract. Toxicol Sci. 42(2):99-108.

Der, S.D., et al. (1997). A double-stranded Rna-activated protein kinase-dependent pathway mediating stress-induced apoptosis. Proc Natl Acad Sci USA. 94(7):3279-3283.

Dudley, D.T., et al. (1995). A synthetic inhibitor of the mitogen-activated protein kinase cascade. Proc Natl Acad Sci USA. 92(17):7686-7689.

Duncan, R., et al. (1991). Conformational and functional analysis of the C-terminal globular head of the reovirus cell attachment protein. Virology. 182(2):810-819.

Duncan, M.R., et al. (1978). Differential sensitivity of normal and transformed human cells to reovirus infection. J Virol. 28(2):444-449.

Gale, Jr., M.J., et al. (1997). Evidence that hepatitis C virus resistance to interferon is mediated through repression of the PKR protein kinase by the nonstructural 5A protein. Virology. 230(2):217-227.

Gentsch, J.R., and Pacitti, A.F. (1985). Effect of neuraminidase treatment of cells and effect of soluble glycoproteins on type 3 reovirus attachment to murine L cells. J Virol. 56(2):356-364.

Gura, T. (1997). Systems for identifying new drugs are often faulty. Science. 278(5340):1041-1042.

Hall-Jackson, C.A., et al. (1998). Induction of cell death by stimulation of protein kinase C in human epithelial cells expressing a mutant ras oncogene: a potential therapeutic target. Br J Cancer. 78(5):641-651.

Hashiro, G., et al. (1977). The preferential cytotoxicity of reovirus for certain transformed cell lines. Arch Virol. 54(4):307-315.

He, B., et al. (1997). Suppression of the phenotype of $_{\gamma 1}$034.5$^-$ herpes simplex virus 1: failure of activated RNA-dependent protein kinase to shut off protein synthesis is associated with a deletion in the domain of the $\alpha$47 gene. J Virol. 71(8):6049-6054.

Helbing, C.C., et al. (1997). A novel candidate tumor suppressor, ING1, is involved in the regulation of apoptosis. Cancer Res. 57(7):1255-1258.

Hershey, J.W. (1991). Translational control in mammalian cells. Annu Rev Biochem. 60:717-755.

Hu, Y., and Conway, T.W. (1993). 2-Aminopurine inhibits the double-stranded RNA-dependent protein kinase both in vitro and in vivo. J Interferon Res. 13(5):323-328.

Ikeda, K., et al. (1999). Oncolytic virus therapy of multiple tumors in the brain requires suppression of innate and elicited antiviral responses. Nat Med. 5(8):881-887.

Ikeda, K., et al. (2000). Complement depletion facilitates the infection of multiple brain tumors by an intravascular, replication-conditional herpes simplex virus mutant. J Virol. 74(10):4765-4775.

Janes, P.W., et al. (1994). Activation of the Ras signalling pathway in human breast cancer cells overexpressing erbB-2. Oncogene. 9(12):3601-3608.

Kawagishi-Kobayashi, M., et al. (1997). Regulation of the protein kinase PKR by the vaccinia virus pseudosubstrate inhibitor K3L is dependent on residues conserved between the K3L protein and the PKR substrate eIF2$\alpha$. Mol Cell Biol. 17(7):4146-4158.

Kirn, D.H., and McCormick, F. (1996). Replicating viruses as selective cancer therapeutics. Mol Med Today. 2(12):519-527.

Kollmorgen, G.M., et al. (1976). Immunotherapy of EL4 lymphoma with reovirus. Cancer Immunol. Immunother. 1:239-244.

Laemmli, U.K. (1970). Cleavage of structural proteins during the assembly of the head of bacteriophage T4. Nature. 227(5259):680-685.

Lee, J.M., and Bernstein, A. (1993). p53 mutations increase resistance to ionizing radiation. Proc Natl Acad Sci USA. 90(12):5742-5746.

Lee, P.W., et al. (1981). Characterization of anti-reovirus immunoglobulins secreted by cloned hybridoma cell lines. Virology. 108(1):134-146.

Levitzki, A. (1994). Signal-transduction therapy. A novel approach to disease management. Eur J Biochem. 226(1):1-13.

Lowe, S.W., et al. (1994). p53 status and the efficacy of cancer therapy in vivo. Science. 266(5186):807-810.

Macara, I.G., et al. (1996). The Ras superfamily of GTPases. FASEB J. 10(5):625-630.

Mah, D.C., et al. (1990). The N-terminal quarter of reovirus cell attachment protein sigma 1 possesses intrinsic virion-anchoring function. Virology. 179(1):95-103.

Marshall, C.J. (1996). Ras effectors. Curr Opin Cell Biol. 8(2):197-204.

McCrae, M.A., and Joklik, W.K. (1978). The nature of the polypeptide encoded by each of the 10 double-stranded RNA segments of reovirus type 3. Virology. 89(2):578-593.

Mills, N. E., et al. (1995). Increased prevalence of K-ras oncogene mutations in lung adenocarcinoma. Cancer Res. 55(7):1444-1447.

Mundschau, L.J., and Faller, D.V. (1992). Oncogenic ras induces an inhibitor of double-stranded RNA-dependent eukaryotic initiation factor 2 $\alpha$-kinase activation. J Biol Chem. 267(32):23092-23098.

Nagata, L., et al. (1984). Molecular cloning and sequencing of the reovirus (serotype 3) S1 gene which encodes the viral cell attachment protein $\sigma$1. Nucleic Acids Res. 12(22):8699-8710.

Paul, R.W., et al. (1989). The $\alpha$-anomeric form of sialic acid is the minimal receptor determinant recognized by reovirus. Virology. 172(1):382-385.

Proud, C.G. (1995). PKR: a new name and new roles. Trends Biochem Sci. 20(6):241-246.

Randazzo, B.P., et al. (1997). Herpes simplex virus 1716, an ICP 34.5 null mutant, is unable to replicate in CV-1 cells due to a translational block that can be overcome by coinfection with SV40. J Gen Virol. 78( Pt 12):3333-3339.

Raybaud-Diogène, H., et al. (1997). Markers of radioresistance in squamous cell carcinomas of the head and neck: a clinicopathologic and immunohistochemical study. J Clin Oncol. 15(3):1030-1038.

Rayter, S.I., et al. (1992). p21ras mediates control of IL-2 gene promoter function in T cell activation. EMBO J. 11(12):4549-4556.

Robinson, M.J., and Cobb, M.H. (1997). Mitogen-activated protein kinase pathways. Curr Opin Cell Biol. 9(2):180-186.

Rosen, L. (1960). Serologic grouping of reoviruses by hemagglutination-inhibition. Am J Hyg. 71:242-249.

Sabin, A.B. (1959). Science in the news. Science 130:966-972.

Samuel, C.E., and Brody, M.S. (1990). Biosynthesis of reovirus-specified polypeptides. 2-aminopurine increases the efficiency of translation of reovirus s1 mRNA but not s4 mRNA in transfected cells. Virology. 176(1):106-113.

Sharp, T.V., et al. (1997). Homologous regions of the α subunit of eukaryotic translational initiation factor 2 (eIF2α) and the vaccinia virus K3L gene product interact with the same domain within the dsRNA-activated protein kinase (PKR). Eur J Biochem. 250(1):85-91.

Smith, R.E., et al. (1969). Polypeptide components of virions, top component and cores of reovirus type 3. Virology. 39(4):791-810.

Soroceanu, L., et al. (1995). Use of genetically engineered HSV-1 viruses in treatment of malignant intracerebral gliomas. FASB J. 9(3):Abstract p. A139.

Stanley, N.F. (1967). Reoviruses. Br Med Bull. 23(2):150-154.

Steele, T.A., and Cox, D.C. (1995). Reovirus type 3 chemoimmunotherapy of murine lymphoma is abrogated by cyclosporine. Cancer Biother. 10(4):307-315.

Strong, J.E., et al. (1993). Evidence that the epidermal growth factor receptor on host cells confers reovirus infection efficiency. Virology. 197(1):405-411.

Strong, J.E., and Lee, P.W. (1996). The v-erbB oncogene confers enhanced cellular susceptibility to reovirus infection. J Virol. 70(1):612-616.

Strong, J.E., et al. (1998). The molecular basis of viral oncolysis: usurpation of the Ras signaling pathway by reovirus. EMBO J. 17(12):3351-3362.

Tang, D. et al. (1993). Recognition of the epidermal growth factor receptor by reovirus. Virology. 197(1):412-414.

Taterka, J., et al. (1995). Characterization of cytotoxic cells from reovirus-infected SCID mice: activated cells express natural killer- and lymphokine-activated killer-like activity but fail to clear infection. J Virol. Jun. 1995;69(6):3910-3914.

Theiss, J.C., et al. (1978). Effect of reovirus infection on pulmonary tumor response to urethan in strain a mice. J Natl Cancer Inst. 61(1):131-134.

Todo, T., et al. (1999). Corticosteroid administration does not affect viral oncolytic activity, but inhibits antitumor immunity in replication-competent herpes simplex virus tumor therapy. Hum Gene Ther. 10(17):2869-2878.

Trimble, W.S., et al. (1986). Inducible cellular transformation by a metallothionein-ras hybrid oncogene leads to natural killer cell susceptibility. Nature. 1986 321(6072):782-784.

Turner, D.L., et al. (1992). Site-directed mutagenesis of the C-terminal portion of reovirus protein σ1: evidence for a conformation-dependent receptor binding domain. Virology. 186(1):219-227.

Umezawa, K., et al. (1994). Isolation of a new vinca alkaloid from the leaves of *Ervatamia microphylla* as an inhibitor of ras functions. Anticancer Res. 14(6B):2413-2417.

Umezawa, K., et al. (1996). Growth inhibition of K-ras-expressing tumours by a new vinca alkaloid, conophylline, in nude mice. Drugs Exp Clin Res. 22(2):35-40.

Waters, S.B., et al. (1995). Desensitization of Ras activation by a feedback disassociation of the SOS-Grb2 complex. J Biol Chem. 270(36):20883-20886.

Wiesmüller, L., and Wittinghofer, F. (1994). Signal transduction pathways involving Ras. Mini review. Cell Signal. 6(3):247-267.

Williams, M.E., et al. (1986). Rejection of reovirus-treated L1210 leukemia cells by mice. Cancer Immunol Immunother. 23(2):87-92.

Wong H. et al. (1994). Monitoring mRNA expression by polymerase chain reaction: the "primer-dropping" method. Anal Biochem. 223(2):251-258.

Yang, Y.L., et al. (1995). Deficient signaling in mice devoid of double-stranded RNA-dependent protein kinase. EMBO J. 14(24):6095-6106.

Yu, D., et al. (1996). Overexpression of c-erbB-2/neu in breast cancer cells confers increased resistance to Taxol via mdr-1-independent mechanisms. Oncogene. 13(6):1359-1365.

Zhang, J.F., et al. (1996). Treatment of a human breast cancer xenograft with an adenovirus vector containing an interferon gene results in rapid regression due to viral oncolysis and gene therapy. Proc Natl Acad Sci USA. 93(9):4513-4518.

Ettinger, "Concurrent paclitaxel-containing regimens and thoracic radiation therapy for limited-disease small cell lung cancer" *Seminars in Radiation Oncology* 9(2 Suppl 1):148-150 (1999) (Abstract Only).

Hirasawa, et al., "Systemic reovirus therapy of metastatic cancer in immune competent mice" *Cancer Research* 63(2):348-353 (2003).

* cited by examiner

METHODS FOR PREVENTING REOVIRUS RECOGNITION FOR THE TREATMENT OF CELLULAR PROLIFERATIVE DISORDERS

BACKGROUND OF THE INVENTION

1. Field of the Invention

The present invention pertains to methods for preventing reovirus recognition in the treatment of cellular proliferative disorders, and particularly ras-mediated cellular proliferative disorders, in mammals. In particular, the methods provide for reovirus treatment of immunosuppressed or immunodeficient mammals to treat the proliferative disorders. Immunosuppression, immunoinhibition or otherwise inducing an immunodeficient state in a mammal renders the reovirus more effective. The methods may include the selective removal of immune constituents that may interfere with the systemic delivery of the virus; preventing reovirus recognition by the host immune system; and removal of the virus from an immune suppressed or immune incompetent host following treatment with reovirus.

REFERENCES

The following publications, patent applications and patents are cited in this application:

U.S. Pat. No. 5,023,252
Armstrong, G. D. et al. (1984), *Virology* 138:37
Aronheiin, A., et al., (1994) *Cell*, 78:949-961
Barbacid, M., *Annu. Rev. Biochem.*, 56:779-827 (1987)
Berrozpe, G., et al. (1994), *Int. J. Cancer,* 58:185-191
Bischoff, J. R. and Samuel, C. E., (1989) *Virology,* 172:106-115
Bos, J. (1989) *Cancer Res.* 49:4682
Cahill, M. A., et al., *Curr. Biol.,* 6:16-19 (1996)
Chandron and Nibert, "Protease cleavage of reovirus capsid protein mul and mulC is blocked by alkyl sulfate detergents, yielding a new type of infectious subvirion particle", *J. of Virology* 72(1):467-75 (1998)
Chaubert, P. et al. (1994), *Am. J. Path.* 144:767
Cuff et al., "Enteric reovirus infection as a probe to study immunotoxicity of the gastrointestinal tract" *Toxicological Sciences* 42(2):99-108 (1998)
Der, S. D. et al., *Proc. Natl. Acad. Sci. USA* 94:3279-3283 (1997)
Dudley, D. T. et al., *Proc. Natl. Acad. Sci. USA* 92:7686-7689 (1995)
Duncan et al., "Conformational and functional analysis of the C-terminal globular head of the reovirus cell attachment protein" *Virology* 182(2):810-9 (1991)
Fields, B. N. et al. (1996), *Fundamental Virology, 3rd Edition,* Lippincott-Raven
Gentsch, J. R. K. and Pacitti, A. F. (1985), *J. Virol.* 56:356
E. Harlow and D. Lane, "Antibodies: A laboratory manual", Cold Spring Harbor Laboratory (1988)
Helbing, C. C. et al., *Cancer Res.* 57.1255-1258 (1997)
Hu, Y. and Conway, T. W. (1993), *J. Interferon Res.,* 13:323-328
James, P. W., et al. (1994) *Oncogene* 9:3601
Laemmli, U. K., (1970) *Nature,* 227:680-685
Lee. J. M. et al. (1993) *PNAS* 90:5742-5746
Lee, P. W. K. et al. (1981) *Virology,* 108:134-146
Lee, P. W. K. et al. (1999) Reovirus for the Treatment of Neoplasia, PCT International Application No. PCT/CA98/00774
Levitzki, A. (1994) *Eur. J. Biochem.* 226:1
Lowe. S. W. et al. (1994) *Science,* 266:807-810
Lyon, H., *Cell Biology, A Laboratory Handbook,* J. E. Celis, ed., Academic Press, 1994, p. 232
Mah et al., "The N-terminal quarter of reovirus cell attachment protein sigma 1 possesses intrinsic virion-anchoring function" *Virology* 179(1):95-103 (1990)
McRae, M. A. and Joklik, W. K., (1978) *Virology,* 89:578-593
Millis, N E et al. (1995) *Cancer Res.* 55:1444
Mundschau, L. J. and Faller, D. V., (1992) *J. Biol. Chem.,* 267:23092-23098
Nagata, L., et al., (1984) *Nucleic Acids Res.,* 12:8699-8710
Paul R. W. et al. (1989) *Virology* 172:382-385
Raybaud-Diogene. H. et al. (1997) *J. Clin. Oncology,* 15(3): 1030-1038
*Remington's Pharmaceutical Sciences,* Mace Publishing Company, Philadelphia Pa. 17$^{th}$ ed. (1985)
Robinson, M. J. and Cobb, M. H., *Curr. Opin. Cell. Biol.* 9:180-186 (1997)
Rosen, L. (1960) *Am. J. Hyg.* 71:242
Sabin, A. B. (1959), *Science* 130:966
Samuel, C. E. and Brody, M., (1990) *Virology,* 176:106-113
Smith, R. E. et al., (1969) *Virology,* 39:791-800
Stanley, N. F. (1967) *Br. Med. Bull.* 23:150
Strong, J. E. et al., (1993) *Virology,* 197:405-411
Strong, J. E. and Lee, P. W. K., (1996) *J. Virol.,* 70:612-616
Trimble, W. S. et al. (1986) *Nature,* 321:782-784
Turner and Duncan, "Site directed mutagenesis of the C-terminal portion of reovirus protein sigmal: evidence for a conformation-dependent receptor binding domain" *Virology* 186(1):219-27 (1992)
Waters, S. D. et al., *J. Biol. Chem.* 270:20883-20886 (1995)
Wiessmuller, L. and Wittinghofer, F. (1994), *Cellular Signaling* 6(3):247-267
Wong, H., et al., (1994) *Anal. Biochem.,* 223:251-258
Yang, Y. L. et al. *EMBO J.* 14:6095-6106 (1995)
Yu, D. et al. (1996) *Oncogene* 13:1359

All of the above publications, patent applications and patents are herein incorporated by reference in their entirety to the same extent as if each individual publication, patent application or patent was specifically and individually indicated to be incorporated by reference in its entirety.

2. State of the Art

Normal cell proliferation is regulated by a balance between growth-promoting proto-oncogenes and growth-constraining tumor-suppressor genes. Tumorigenesis can be caused by genetic alterations to the genome that result in the mutation of those cellular elements that govern the interpretation of cellular signals, such as potentiation of proto-oncogene activity or inactivation of tumor suppression. It is believed that the interpretation of these signals ultimately influences the growth and differentiation of a cell, and that misinterpretation of these signals can result in neoplastic growth (neoplasia).

Genetic alteration of the proto-oncogene Ras is believed to contribute to approximately 30% of all human tumors (Wiessmuller, L. and Wittinghofer, F. (1994), *Cellular Signaling* 6(3):247-267; Barbacid, M. (1987) *A Rev. Biochem.* 56, 779-827). The role that Ras plays in the pathogenesis of human tumors is specific to the type of tumor. Activating mutations in Ras itself are found in most types of human malignancies, and are highly represented in pancreatic cancer (80%), sporadic colorectal carcinomas (40-50%), human lung adenocarcinomas (15-24%), thyroid tumors (50%) and myeloid leukemia (30%) (Millis, N E et al. (1995) *Cancer Res.* 55:1444; Chaubert, P. et al. (1994), *Am. J. Path.* 144:767; Bos, J. (1989) *Cancer Res.* 49:4682). Ras activation is also demonstrated by upstream mitogenic signaling elements, notably by tyrosine receptor kinases (RTKs). These upstream elements, if amplified or overexpressed, ultimately result in elevated Ras activity by the signal transduction activity of Ras. Examples of this include overexpression of PDGFR in certain forms of glioblastomas, as well as in c-erbB-2/neu in breast cancer (Levitzki, A. (1994) *Eur. J. Biochem.* 226:1; James, P. W., et al. (1994) *Oncogene* 9:3601; Bos, J. (1989) *Cancer Res.* 49:4682).

Current methods of treatment for neoplasia include surgery, chemotherapy and radiation. Surgery is typically used as the primary treatment for early stages of cancer; however, many tumors cannot be completely removed by surgical means. In addition, metastatic growth of neoplasms may prevent complete cure of cancer by surgery. Chemotherapy involves administration of compounds having antitumor activity, such as alkylating agents, antimetabolites, and antitumor antibiotics. The efficacy of chemotherapy is often limited by severe side effects, including nausea and vomiting, bone marrow depression, renal damage, and central nervous system depression. Radiation therapy relies on the greater ability of normal cells, in contrast with neoplastic cells, to repair themselves after treatment with radiation. Radiotherapy cannot be used to treat many neoplasms, however, because of the sensitivity of tissue surrounding the tumor. In addition, certain tumors have demonstrated resistance to radiotherapy and such may be dependent on oncogene or anti-oncogene status of the cell (Lee. J. M. et al. (1993) *PNAS* 90:5742-5746; Lowe. S. W. et al. (1994) *Science*, 266:807-810; Raybaud-Diogene. H. et al. (1997) *J. Clin. Oncology*, 15(3): 1030-1038). In view of the drawbacks associated with the current means for treating neoplastic growth, the need still exists for improved methods for the treatment of most types of cancers.

SUMMARY OF THE INVENTION

The present invention is directed to the enhancement of the effectiveness of existing reovirus therapies in the treatment of proliferative disorders.

This invention pertains to methods for preventing reovirus recognition in the treatment of cellular proliferative disorders, and particularly ras-mediated cellular proliferative disorders, in mammals. The mammal may be selected from dogs, cats, sheep, goats, cattle, horses, pigs, mice, humans and non-human primates. The method comprises suppressing or otherwise inhibiting the immune system of the mammal and, concurrently or subsequently, administering to the proliferating cells an effective amount of one or more reoviruses under conditions which result in substantial lysis of the proliferating cells. In particular, the methods provide for reovirus treatment of immunosuppressed or immunodeficient mammals to treat the proliferative disorders. Immunosuppression, immunoinhibition or otherwise inducing an immunodeficient state in a mammal renders the reovirus more effective. The methods may include the selective removal of immune constituents that may interfere with the systemic delivery of the virus; preventing reovirus recognition by the host immune system; and removal of the virus from an immune suppressed or immune incompetent host following treatment with reovirus. Alternatively, reovirus may be administered to a mammal with a diminished immune response system under conditions which result in substantial lysis of the proliferating cells. Immune systems may be compromised by one or more of the following: an HIV infection; as a side effect of chemotherapy or radiation therapy; by selective removal of B and/or T cell populations; by removal of antibodies (anti-antireovirus antibodies or all antibodies), and the like.

The immunosuppression or immunoinhibition may be accomplished by means of an immunosuppressant, an immune suppressive agent, or by any other means which inhibits a mammal's immune system or renders the mammal immunodeficient. When an immunosuppressant is used, it may be administered prior to or concurrent with reovirus administration. The mammal should be rendered immunosuppressed, immunodeficient or immunoinhibited prior to or concurrent with reovirus administration.

The reovirus may be a mammalian reovirus or an avian reovirus. The reovirus may be modified such that the outer capsid is removed, the virion is packaged in a liposome or micelle or the proteins of the outer capsid have been mutated. The reovirus and/or immunosuppressive agent can be administered in a single dose or in multiple doses. The proliferative disorder may be a neoplasm. Both solid and hematopoietic neoplasms can be targeted. The immunosuppression results in more effective reovirus treatment.

Accordingly, in one aspect the invention provides a method of treating a ras-mediated proliferative disorder in a mammal, comprising the steps of:
  a) performing a step selected from the group consisting of:
   i) administering to the proliferating cells in said mammal an effective amount of an immune suppressive agent;
   ii) removing B-cells or T-cells from said mammal;
   iii) removing anti-reovirus antibodies from said mammal;
   iv) removing antibodies from said mammal;
   v) administering anti-antireovirus antibodies to said mammal; and
   vi) suppressing the immune system of the mammal; and
  b) administering to the proliferating cells in said mammal an effective amount of one or more reoviruses under conditions which result in substantial lysis of the proliferating cells.

Also provided is a method of treating a ras-mediated neoplasm in a human, comprising suppressing or otherwise compromising the immune system of the mammal and, concurrently or subsequently, administering to the neoplasm a reovirus in an amount sufficient to result in substantial oncolysis of the neoplastic cells. The reovirus may be administered by injection into or near a solid neoplasm.

Also provided is a method of inhibiting metastasis of a neoplasm in a mammal, comprising suppressing or otherwise compromising the immune system of the mammal and, concurrently or subsequently, administering to the mammal a reovirus in an amount sufficient to result in substantial lysis of the neoplastic cells.

Also provided is a method of treating a suspected ras-mediated neoplasm in a mammal, comprising surgical removal of the substantially all of the neoplasm, suppression or other inhibition of the immune system of the mammal and, administration of an effective amount of reovirus at or near to the surgical site resulting in oncolysis of any remaining neoplastic cells.

Also provided is a pharmaceutical composition comprising an immunosuppressant or an immunoinhibitant such as an anti-antireovirus antibody, a reovirus, and a pharmaceutically acceptable excipient.

Kits comprising a reovirus and another component such as an immune suppressive agent, means for removing B-cells or T-cells from a mammal, means for removing anti-reovirus antibodies from a mammal, means for removing antibodies from a mammal, anti-antireovirus antibodies and means for suppressing the immune system of the mammal are also provided.

Also provided is a pharmaceutical composition comprising an immunosuppressant or immunoinhibitant, a modified reovirus and a pharmaceutically acceptable excipient.

The methods and pharmaceutical compositions of the invention provide an effective means to treat neoplasia, without the side effects associated with other forms of cancer therapy. Inhibition or suppression of the immune system increases the availability of reovirus to infect and lyse ras-mediated proliferating cells because anti-reovirus antibodies are not formed. Because reovirus is not known to be associated with disease, any safety concerns associated with deliberate administration of a virus are minimized.

The foregoing and other objects, features and advantages of the invention will be apparent from the following more particular description of preferred embodiments of the invention, as illustrated in the accompanying drawings.

DETAILED DESCRIPTION OF THE INVENTION

We have demonstrated the human reovirus requires an activated Ras signaling pathway for infection of cultured cells (Strong, J E et al 1998 EMBO J. 17: 3351). Further, we have demonstrated that reovirus could be used as an oncolytic agent in a number of animal models (Lee, P. W. K. et al (1999)). Severe combined immune deficient mice (SCID) mice bearing tumors established from v-erbB-transformed murine NIH 3T3 cells or human U87 glioblastomas cells were is treated with the virus (Coffey, M C et al 1998 Science 282: 1332). A single intratumoral injection of virus resulted in regression of tumor. We have further demonstrated that in animals given bilateral U87 tumor xenografts that a single unilateral injection of reovirus into the ipsilateral tumor resulted in reduction in the contralateral tumor. This reduction in the remote tumor site is the result of systemic spread of the virus. To examine the effect that a functional immune system could play upon this type of therapy, an immune competent mouse model was established. Treatment of immune-competent C3H mice bearing tumors established from ras-transformed C3H-10T1/2 cells also resulted in tumor regression, although a series of injections was required (Coffey, M C et al 1998). Thus, co-administration of the virus with an immune suppressive agent, or to an animal with a diminished immune response, allows a reduction in the concentration and/or frequency of reovirus treatments. Further, immune suppression of the animal may improve response rates in synchronous ras mediated lesions remote from the tumor injected or alternatively when delivered systemically. Immune suppression may also aid in systemic delivery by increasing the bioavailable virus.

The invention pertains to methods of treating a ras-mediated proliferative disorder in a mammal, by immunosuppressing, immunoinhibiting or otherwise rendering the mammal immunodeficient and, concurrently or subsequently, administering reovirus to the proliferating cells.

The name reovirus (Respiratory and enteric orphan virus) is a descriptive acronym suggesting that these viruses, although not associated with any known disease state in humans, can be isolated from both the respiratory and enteric tracts (Sabin, A. B. (1959), Science 130:966). The term "reovirus" refers to all viruses classified in the reovirus genus.

Reoviruses are viruses with a double-stranded, segmented RNA genome. The virions measure 60-80 nm in diameter and possess two concentric capsid shells, each of which is icosahedral. The genome consists of double-stranded RNA in 10-12 discrete segments with a total genome size of 16-27 kbp. The individual RNA segments vary in size. Three distinct but related types of reovirus have been recovered from many species. All three types share a common complement-fixing antigen.

The human reovirus consists of three serotypes: type 1 (strain Lang or T1L), type-2 (strain Jones, T2J) and type 3 (strain Dearing or strain Abney, T3D). The three serotypes are easily identifiable on the basis of neutralization and hemagglutinin-inhibition assays (Sabin, A. B. (1959), Science 130: 966; Fields, B. N. et al. (1996), Fundamental Virology. 3rd Edition, Lippincott-Raven; Rosen, L. (1960) Am. J. Hyg. 71:242; Stanley, N. F. (1967) Br. Med. Bull. 23:150).

Although reovirus is not known to be associated with any particular disease, many people have been exposed to reovirus by the time they reach adulthood (i.e., fewer than 25% in children <5 years old, to greater than 50% in those 20-30 years old (Jackson G. G. and Muldoon R. L. (1973) J. Infect. Dis. 128:811; Stanley N. F. (1974) In: Comparative Diagnosis of Viral Diseases, edited by E. Kurstak and K. Kurstak, 385421, Academic Press, New York).

For mammalian reoviruses, the cell surface recognition signal is sialic acid (Armstrong, G. D. et al. (1984), Virology 138:37; Gentsch, J. R. K. and Pacitti, A. F. (1985), J. Virol. 56:356; Paul R. W. et al. (1989) Virology 172:382-385) Due to the ubiquitous nature of sialic acid, reovirus binds efficiently to a multitude of cell lines and as such can potentially target many different tissues; however, there are significant differences in susceptibility to reovirus infection between cell lines.

As described herein, Applicants have discovered that cells which are resistant to reovirus infection became susceptible to reovirus infection when transformed by a gene in the Ras pathway. "Resistance" of cells to reovirus infection indicates that infection of the cells with the virus did not result in significant viral production or yield. Cells that are "susceptible" are those that demonstrate induction of cytopathic effects, viral protein synthesis, and/or virus production. Resistance to reovirus infection was found to be at the level of gene translation, rather than at early transcription: while viral transcripts were produced, virus proteins were not expressed. Without being limited to a theory, it is thought that viral gene transcription in resistant cells correlated with phosphorylation of an approximately 65 kDa cell protein, determined to be double-stranded RNA-activated protein kinase (PKR), that was not observed in transformed cells. Phosphorylation of PKR lead to inhibition of translation. When phosphorylation was suppressed by 2-aminopurine, a known inhibitor of PKR, drastic enhancement of reovirus protein synthesis occurred in the untransformed cells. Furthermore, a severe combined immunodeficiency (SCID) mouse model in which tumors were created on both the right and left hind flanks revealed that reovirus significantly reduced tumor size when injected directly into the right-side tumor; in addition, significant reduction in tumor size was also noted on the left-side tumor which was not directly injected with reovirus, indicating that the oncolytic capacity of the reovirus was systemic as well as local.

While reovirus may effectively be used to treat neoplasia in immunocompetent mice, we have found that larger numbers (about ten-fold) of reovirus and multiple treatments may be required for best effect. Further, intratumoral injection may be needed for maximum effect in immunocompetent animals.

These results indicated that reovirus uses the host cell's Ras pathway machinery to downregulate PKR and thus reproduce. For both untransformed (reovirus-resistant) and EGFR-, Sos-, or ras-transformed (reovirus-susceptible) cells, virus binding, internalization, uncoating, and early transcription of viral genes all proceed normally. In the case of untransformed cells, secondary structures on the early viral transcripts inevitably trigger the phosphorylation of PKR, thereby activating it, leading to the phosphorylation of the translation initiation factor eIF-2α, and hence the inhibition of viral gene translation. In the case of EGFR-, Sos-, or ras-transformed cells, the PKR phosphorylation step is prevented or reversed by Ras or one of its downstream elements, thereby allowing viral gene translation to ensue. The action of Ras (or a downstream element) can be mimicked by the use of 2-aminopurine (2-AP), which promotes viral gene translation (and hence reovirus infection) in untransformed cells by blocking PKR phosphorylation.

The implantation of human tumor cells into SCID mice is recognized as a well known model system for testing the effectiveness of various anti-tumor agents in humans. It has previously been shown that pharmaceuticals effective against human tumors implanted into SCID mice are predictive of their effectiveness against the same tumors in humans.

Based upon these discoveries, Applicants have developed methods for treating ras-mediated proliferative disorders in mammals. Representative mammals include dogs, cats, sheep, goats, cattle, horses, pigs, mice, non-human primates, and humans. In a preferred embodiment, the mammal is a human.

In the methods of the invention, reovirus is administered to Ras-mediated proliferating cells in the individual mammal. In one embodiment of this invention a course of reovirus therapy is administered one or more times. Following the first administration of reovirus therapy particular immune constituents that may interfere with subsequent administrations of reovirus are removed from the patient. These immune constituents include B cells, T cells, antibodies, and the like.

Removal of either the B cell or T cell population can be accomplished by several methods. In one method, the blood may be filtered and heme-dialysis may be performed. Another method is the filtration of the blood coupled with extra corporeal compounds that can remove the cell populations, for example, with immobilized antibodies that recognize specific receptors on the cell population which is to be remove. Yet another method for removal of a cell population is by immune suppression. This can be done by first line radiation therapy or by cyclic steroids such as cyclosporin.

Selective removal of anti-reovirus antibodies can also prevent the patient's immune system from removing therapeutically administered reovirus. Preventing antibody interaction with the virus may also assist systemic treatment strategies. Antibodies can be removed by several methods, including heme-dialysis and passing the blood over immobilized reovirus (selective antibody removal); by removal of all IgG antibodies by heme-dialysis and passing the blood over immobilized protein A (commercially available as PROSORBA, Cypress Bioscience, San Diego, Calif.); or by administration of humanized anti-idiotypic antibodies, where the idiotype is against reovirus Another method of this invention is to allow reovirus to act systemically without impairing normal immune function by masking or impairing immune recognition of reovirus. To prevent the patient's immune system from recognizing reovirus, another embodiment of this invention is the serial administration of reovirus and reovirus reassortants. Alternatively, the reovirus may be coated with non-virotoxic humanized antibodies, such as coating with the $F_{ab}$ portion of the antibody, or coated in a micelle.

Additionally, the virus may be treated with chymotrypsin to yield an infectious subviral particle (ISVP). An ISVP may be used either alone or in combination with whole virus to provide an agent that is either poorly recognized has not been previously prevented by the patient's immune system.

Another embodiment of this invention includes the removal of reovirus from the patient following administration. Since this method may be used on patients that are either immune suppressed or immune incompetent, it may be of importance to remove virus from the blood stream following the course of treatment. Reovirus may be removed by affinity chromatography using extra corporeal anti-reovirus antibodies associated with heme dialysis, B-cell proliferative agents, or adjuvants to stimulate immune response against the virus such as UV inactivated virus or Freund's adjuvant.

In the methods of the invention, reovirus is administered to ras-mediated proliferating cells in the individual mammal. Representative types of human reovirus that can be used include type 1 (e.g., strain Lang or TIL); type 2 (e.g., strain Jones or T2J); and type 3 (e.g., strain Dearing or strain Abney, T3D or T3A); other strains of reovirus can also be used. In a preferred embodiment, the reovirus is human reovirus serotype 3, more preferably the reovirus is human reovirus serotype 3, strain Dearing. Alternatively, the reovirus can be a non-human mammalian reovirus (e.g., non-human primate reovirus, such as baboon reovirus; equine; or canine reovirus), or a non-mammalian reovirus (e.g., avian reovirus). A combination of different serotypes and/or different strains of reovirus, such as reovirus from different species of animal, can be used.

The reovirus may be naturally occurring or modified. The reovirus is "naturally-occurring": when it can be isolated from a source in nature and has not been intentionally modified by humans in the laboratory. For example, the reovirus can be from a "field source": that is, from a human patient.

The reovirus may be modified but still capable of lytically infecting a mammalian cell having an active ras pathway. The reovirus may be chemically or biochemically pretreated (e.g., by treatment with a protease, such as chymotrypsin or trypsin) prior to administration to the proliferating cells. Pretreatment with a protease removes the outer coat or capsid of the virus and may increase the infectivity of the virus. The reovirus may be coated in a liposome or micelle (Chandron and Nibert, "Protease cleavage of reovirus capsid protein mul and mulC is blocked by alkyl sulfate detergents, yielding a new type of infectious subvirion particle", J. of Virology 72(1):467-75 (1998)) to reduce or prevent an immune response from a mammal which has developed immunity to the reovirus. For example, the virion may be treated with chymotrypsin in the presence of micelle forming concentrations of alkyl sulfate detergents to generate a new infectious subvirion particle.

The reovirus may be a recombinant reovirus from two or more types of reoviruses with differing pathogenic phenotypes such that it contains different antigenic determinants thereby reducing or preventing an immune response by a mammal previously exposed to a reovirus subtype. Such recombinant virions, also known as reassortants, can be generated by co-infection of mammalian cells with different subtypes of reovirus with the resulting resorting and incorporation of different subtype coat proteins into the resulting virion capsids.

The reovirus may be modified by incorporation of mutated coat proteins, such as for example σ1, into the virion outer capsid. The proteins may be mutated by replacement, insertion or deletion. Replacement includes the insertion of different amino acids in place of the native amino acids. Insertions include the insertion of additional amino acid residues into the protein at one or more locations. Deletions include deletions of one or more amino acid residues in the protein. Such mutations may be generated by methods known in the art. For example, oligonucleotide site directed mutagenesis of the gene encoding for one of the coat proteins could result in the generation of the desired mutant coat protein. Expression of the mutated protein in reovirus infected mammalian cells in vitro such as COS1 cells will result in the incorporation of the mutated protein into the reovirus virion particle (Turner and Duncan, "Site directed mutagenesis of the C-terminal portion of reovirus protein sigmal: evidence for a conformation-dependent receptor binding domain" *Virology* 186(1):219-27 (1992); Duncan et al., "Conformational and functional analysis of the C-terminal globular head of the reovirus cell attachment protein" *Virology* 182(2):810-9 (1991); Mah et al., "The N-terminal quarter of reovirus cell attachment protein sigma 1 possesses intrinsic virion-anchoring function" *Virology* 179 (1):95-103 (1990))

The reovirus is preferably a reovirus modified to reduce or eliminate an immune reaction to the reovirus. Such modified reovirus are termed "immunoprotected reovirus". Such modifications could include packaging of the reovirus in a liposome, a micelle or other vehicle to mask the reovirus from the mammals immune system. Alternatively, the outer capsid of the reovirus virion particle may be removed since the proteins present in the outer capsid are the major determinant of the host humoral and cellular responses.

A "proliferative disorder" is any cellular disorder in which the cells proliferate more rapidly than normal tissue growth. Thus a "proliferating cell" is a cell that is proliferating more rapidly than normal cells. The proliferative disorder, includes but is not limited to neoplasms. A neoplasm is an abnormal tissue growth, generally forming a distinct mass, that grows by cellular proliferation more rapidly than normal tissue growth. Neoplasms show partial or total lack of structural organization and functional coordination with normal tissue.

These can be broadly classified into three major types. Malignant neoplasms arising from epithelial structures are called carcinomas, malignant neoplasms that originate from connective tissues such as muscle, cartilage, fat or bone are called sarcomas and malignant tumors affecting hematopoietic structures (structures pertaining to the formation of blood cells) including components of the immune system, are called leukemias and lymphomas. A tumor is the neoplastic growth of the disease cancer. As used herein, a "neoplasm", also referred to as a "tumor", is intended to encompass hematopoietic neoplasms as well as solid neoplasms. Other proliferative disorders include, but are not limited to neurofibromatosis.

At least some of the cells of the proliferative disorder have a mutation in which the Ras gene (or an element of the Ras signaling pathway) is activated, either directly (e.g., by an activating mutation in Ras) or indirectly (e.g., by activation of an upstream element in the Ras pathway). Activation of an upstream element in the Ras pathway includes, for example, transformation with epidermal growth factor receptor (EGFR) or Sos. A proliferative disorder that results, at least in part, by the activation of Ras, an upstream element of Ras, or an element in the Ras signaling pathway is referred to herein as a "Ras-mediated proliferative disorder".

"B-cells" refers to B-lymphocytes. There are two major subpopulations of B lymphocytes, B-1 and B-2 cells. B-1 cells are self-renewing and frequently secrete high levels of antibody which binds to a range of antigens (polyspecificity) with a relatively low affinity. The majority of B cells, B-2 cells, are directly generated from precursors in the bone marrow and secrete highly specific antibody.

"T-cells" refers to T-lymphocytes. T-cells differentiate within the thymus gland and are specialized to operate against cells bearing intracellular organisms. T-cells only recognize antigen when it is on the surface of a body cell.

"Anti-reovirus antibody" refers to an antibody which binds to reovirus. "IgG antibodies" refers to immunoglobulin G antibodies. IgG, the most abundant type of antibody, carries the major burden of neutralizing bacterial toxins and binding to microorganisms to enhance their phagocytosis. "Humanized antibodies" refers to antibody molecules in which the amino acid sequence in the non-antigen binding regions has been altered so that the antibody more closely resembles a human antibody, and still retains its original binding ability.

One neoplasm that is particularly susceptible to treatment by the methods of the invention is pancreatic cancer, because of the prevalence of Ras-mediated neoplasms associated with pancreatic cancer. Other neoplasms that are particularly susceptible to treatment by the methods of the invention include breast cancer, central nervous system cancer (e.g., neuroblastoma and glioblastoma), peripheral nervous system cancer, lung cancer, prostate cancer, colorectal cancer, thyroid cancer, renal cancer, adrenal cancer, liver cancer, lymphoma and leukemia. One proliferative disorder that is particularly susceptible to treatment by the methods of this invention include neurofibromatosis 1 because of the activation of the ras pathway.

"Administration to a proliferating cell or neoplasm" indicates that the reovirus is administered in a manner so that it contacts the proliferating cells or cells of the neoplasm (also referred to herein as "neoplastic cells"). The route by which the reovirus is administered, as well as the formulation, carrier or vehicle, will depend on the location as well as the type of the neoplasm. A wide variety of administration routes can be employed. For example, for a solid neoplasm that is accessible, the reovirus can be administered by injection directly to the neoplasm. For a hematopoietic neoplasm, for example, the reovirus can be administered intravenously or intravascularly. For neoplasms that are not easily accessible within the body, such as metastases or brain tumors, the reovirus is administered in a manner such that it can be transported systemically through the body of the mammal and thereby reach the neoplasm (e.g., intrathecally, intravenously or intramuscularly). Alternatively, the reovirus can be administered directly to a single solid neoplasm, where it then is carried systemically through the body to metastases. The reovirus can also be administered subcutaneously, intraperitoneally, topically (e.g., for melanoma), orally (e.g., for oral or esophageal neoplasm), rectally (e.g., for colorectal neoplasm), vaginally (e.g., for cervical or vaginal neoplasm), nasally or by inhalation spray (e.g., for lung neoplasm).

Reovirus can be administered systemically to mammals which are immune compromised or which have not developed immunity to the reovirus epitopes. In such cases, reovirus administered systemically, i.e. by intraveneous injection, will contact the proliferating cells resulting in lysis of the cells.

Immunocompetent mammals previously exposed to a reovirus subtype may have developed humoral and/or cellular immunity to that reovirus subtype. Nevertheless, it has been found that direct injection of the reovirus into a solid tumor in immunocompetent mammals will result in the lysis of the neoplastic cells. On the other hand, when the reovirus is administered systemically to immunocompetent mammals, the mammals may produce an immune response to the reovirus. Such an immune response may be avoided if the reovirus is of a subtype to which the mammal has not developed immunity, or the reovirus has been modified as previously described herein such that it is immunoprotected, for example, by protease digestion of the outer capsid or packaging in a micelle.

Alternatively, it is contemplated that the immunocompetency of the mammal against the reovirus may be suppressed either by the prior or co-administration of pharmaceuticals known in the art to suppress the immune system in general (Cuff et al., "Enteric reovirus infection as a probe to study immunotoxicity of the gastrointestinal tract" *Toxicological Sciences* 42(2):99-108 (1998)) or alternatively the administration of such immunoinhibitors as anti-antireovirus antibodies. The humoral immunity of the mammal against reovirus may also be temporarily reduced or suppressed by plasmaphoresis of the mammals blood to remove the antireovirus antibodies. The humoral immunity of the mammal against reovirus may additionally be temporarily reduced or suppressed by the intraveneous administration of non-specific immunoglobulin to the mammal.

It is contemplated that the reovirus may be administered to immunocompetent mammals immunized against the reovirus in conjunction with the administration of immunosuppressants and/or immunoinhibitors. Such immunosuppressants and immunoinhibitors are known to those of skill in the art and include such agents as cyclosporin, rapamycin, tacrolimus, mycophenolic acid, azathioprine and their analogs, and the like. Other agents are known to have immunosuppressant properties as well (see, e.g., Goodman and Gilman, $7^{th}$ Edition, page 1242, the disclosure of which is incorporated herein by reference). Such immunoinhibitors also include "anti-antireovirus antibodies," which are antibodies directed against anti-reovirus antibodies. Such antibodies can be made by methods known in the art. See for example "Antibodies: A laboratory manual" E. Harlow and D. Lane, Cold Spring Harbor Laboratory (1988). Such anti-antireovirus antibodies may be administered prior to, at the same time or shortly after the administration of the reovirus. Preferably an effective amount of the anti-antireovirus antibodies are administered in sufficient time to reduce or eliminate an immune response by the mammal to the administered reovirus. The terms "immunosuppressant" or "immune suppressive agent" include conventional immunosuppressants, immunoinhibitors, antibodies, and conditions such as radiation therapy or HIV infection which result in compromise of the immune system.

The term "substantial lysis" means at least 10% of the proliferating cells are lysed, more preferably of at least 50% and most preferably of at least 75% of the cells are lysed. The percentage of lysis can be determined for tumor cells by measuring the reduction in the size of the tumor in the mammal or the lysis of the tumor cells in vitro.

A "mammal suspected of having a proliferative disorder" means that the mammal may have a proliferative disorder or tumor or has been diagnosed with a proliferative disorder or tumor or has been previously diagnosed with a proliferative disorder or tumor, the tumor or substantially all of the tumor has been surgically removed and the mammal is suspected of harboring some residual tumor cells.

This invention also includes pharmaceutical compositions which contain, as the active ingredient, one or more immunosuppressants or immunoinhibitors and one or more of the reoviruses associated with "pharmaceutically acceptable carriers or excipients". In making the compositions of this invention, the active ingredients/immunosuppressant or immunoinhibitor and reovirus are usually mixed with an excipient, diluted by an excipient or enclosed within such a carrier which can be in the form of a capsule, sachet, paper or other container. When the pharmaceutically acceptable excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

For preparing solid compositions such as tablets, the principal active ingredients/immunosuppressant or immunoinhibitor and reovirus are mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

Another preferred formulation employed in the methods of the present invention employs transdermal delivery devices ("patches"). Such transdermal patches may be used to provide continuous or discontinuous infusion of the reovirus of the present, invention in controlled amounts. The construction and use of transdermal patches for the delivery of pharmaceutical agents is well known in the art. See, for example, U.S. Pat. No. 5,023,252, herein incorporated by reference. Such patches may be constructed for continuous, pulsatile, or on demand delivery of pharmaceutical agents.

Other suitable formulations for use in the present invention can be found in *Remington's Pharmaceutical Sciences*, the disclosure of which is incorporated herein by reference.

The immunosuppressant or immunoinhibitor and reovirus or the pharmaceutical composition comprising the immunosuppressant or immunoinhibitor and reovirus may be packaged into convenient kits providing the necessary materials packaged into suitable containers. It is contemplated the kits may also include chemotherapeutic agent.

The immunosuppressant or immunoinhibitor is administered in an appropriate amount and using an appropriate schedule of administration sufficient to result in immunosuppression or immunoinhibition of the mammal's immune system. Such amounts and schedules are well known to those of skill in the art.

The reovirus is administered in an amount that is sufficient to treat the proliferative disorder (e.g., an "effective amount"). A proliferative disorder is "treated" when administration of reovirus to the proliferating cells effects lysis of the proliferating cells. This may result in a reduction in size of the neoplasm, or in a complete elimination of the neoplasm. The reduction in size of the neoplasm, or elimination of the neoplasm, is generally caused by lysis of neoplastic cells ("oncolysis") by the reovirus. Preferably the effective amount is that amount able to inhibit tumor cell growth. Preferably the effective amount is from about 1.0 pfu/kg body weight to about $10^{15}$ pfu/kg body weight, more preferably from about $10^2$ pfu/kg body weight to about $10^{13}$ pfu/kg body weight. For example, for treatment of a human, approximately $10^2$ to $10^{17}$ plaque forming units (PFU) of reovirus can be used, depending on the type, size and number of tumors present. The effective amount will be determined on an individual basis and may be based, at least in part, on consideration of the type of reovirus; the chosen route of administration; the individual's size, age, gender; the severity of the patient's symptoms; the size and other characteristics of the neoplasm; and the like. The course of therapy may last from several days to several months or until diminution of the disease is achieved.

The immunosuppressant or immunoinhibitor and reovirus can be administered in a single dose, or multiple doses (i.e., more than one dose). The multiple doses can be administered concurrently, or consecutively (e.g., over a period of days or weeks). The reovirus can also be administered to more than one neoplasm in the same individual.

The compositions are preferably formulated in a unit dosage form, each dosage containing an appropriate amount of immunosuppressant or immunoinhibitor and from about $10^2$ pfus to about $10^{13}$ pfus of the reovirus. The term "unit dosage forms" refers to physically discrete units suitable as unitary dosages for human subjects and other mammals, each unit containing a predetermined quantity of reovirus calculated to produce the desired therapeutic effect, in association with a suitable pharmaceutical excipient.

As mentioned above, it has been found that the reovirus is effective for the treatment of solid neoplasms in immunocompetent mammals. Administration of unmodified reovirus directly to the neoplasm results in oncolysis of the neoplastic cells and reduction in the size of the tumor in immunocompetent animals. When animals are rendered immunosuppressed or immunodeficient in some way, systemic administration of reovirus will be more effective in producing oncolysis.

It is contemplated that the reovirus may be administered in conjunction with surgery or removal of the neoplasm. Therefore, provided herewith are methods for the treatment of a solid neoplasm comprising surgical removal of the neoplasm and administration of a reovirus at or near to the site of the neoplasm.

It is contemplated that the reovirus may be administered in conjunction with or in addition to radiation therapy which renders the mammal immunosuppressed.

It is further contemplated that the reovirus of the present invention may be administered in conjunction with or in addition to known anticancer compounds or chemotherapeutic agents. Chemotherapeutic agents are compounds which may inhibit the growth of tumors. Such agents, include, but are not limited to, 5-fluorouracil, mitomycin C, methotrexate, hydroxyurea, cyclophosphamide, dacarbazine, mitoxantrone, anthracyclins (Epirubicin and Doxurubicin), antibodies to receptors, such as herceptin, etopside, pregnasome, platinum compounds such as carboplatin and cisplatin, taxanes such as taxol and taxotere, hormone therapies such as tamoxifen and anti-estrogens, interferons, aromatase inhibitors, progestational agents and LHRH analogs.

The reovirus and immunosuppressants of the present invention have been found to reduce the growth of tumors that are metastatic. In an embodiment of the invention, a method is provided for reducing the growth of metastatic tumors in a mammal comprising administering an effective amount of a reovirus to the immunosuppressed mammal.

Utility

The reoviruses and immunosuppressants of the present invention may be used for a variety of purposes. They may be used in methods for treating ras-mediated proliferative disorders in a mammal. They may be used to reduce or eliminate neoplasms. They may be used in methods for treating metastases. They may be used in conjunction with known treatments for cancer including surgery, chemotherapy and radiation.

In order to further illustrate the present invention and advantages thereof, the following specific examples are given but are not meant to limit the scope of the claims in any way.

EXAMPLES

In the examples below, all temperatures are in degrees Celsius (unless otherwise indicated) and all percentages are weight percentages (also unless otherwise indicated).

In the examples below, the following abbreviations have the following meanings. If an abbreviation is not defined, it has its generally accepted meaning:

=micromolar
mM=millimolar
M=molar
ml=milliliter
µl=microliter
mg=milligram
µg=microgram
PAGE=polyacrylamide gel electrophoresis
rpm=revolutions per minute
FBS=fetal bovine serum
DTT=dithiothrietol
SDS=sodium dodecyl sulfate PBS=phosphate buffered saline
DMEM=Dulbecco's modified Eagle's medium
α-MEM=α-modified Eagle's medium
β-ME=β-mercaptoethanol
MOI=multiplicity of infection
PFU plaque forming units
MAPK=MAP kinase
phosph-MAPK=phosphorylated-MAP kinase
HRP=horseradish-peroxidase
PKR=double-stranded RNA activated protein kinase
RT-PCR=reverse transcriptase-polymerase chain reaction
GAPDH=glyceraldehyde-3-phosphate dehydrogenase
EGFR=epidermal growth factor receptors
MEK kinase=mitogen-activated extracellular signal-regulated kinase
DMSO=dimethylsulfoxide
SCID=severe combined immunodeficiency General Methods Cells and Virus Parental NIH-3T3 and NIH-3T3 cells transfected with the Harvey-ras (H-ras) and EJ-ras oncogenes were a generous gift of Dr. Douglas Faller (Boston University School of Medicine). NIH-3T3 cells along with their Sos-transformed counterparts (designated TNIH#5) were a generous gift of Dr. Michael Karin (University of California, San Diego). Dr. H.-J. Kung (Case Western Reserve University) kindly donated parental NIH-3T3 cells along with NIH-3T3 cells transfected with the v-erbB oncogene (designated THC-11), 2H1 cells, a derivative of the C3H 10T1/2 murine fibroblast line, containing the Harvey-ras gene under the transcriptional control of the mouse metallothionein-I promoter were obtained from Dr. Nobumichi Hozurmi (Mount Sinai Hospital Research Institute). These 2H1 cells are conditional ras transformant that express the H-ras oncogene in the presence of 50 μM $ZnSO_4$. All cell lines were grown in Dulbecco's modified Eagle's medium (DMEM) containing 10% fetal bovine serum (FBS).

The NIH-3T3 tet-myc cells were obtained from Dr. R. N. Johnston (University of Calgary) and were grown in DMEM containing 10% heat-inactivated FBS and antibiotics in the presence or absence of 2 μg/ml tetracycline (Helbing, C. C. et al., Cancer Res. 57:1255-1258 (1997)). In the presence of tetracycline, expression of the human c-myc gene is repressed. Removal of tetracycline results in the elevation of expression of c-myc by up to 100-fold in these cells, which also display a transformed phenotype.

The $PKR^{+/+}$ and $PKR^{°/°}$ mouse embryo fibroblasts (MEFs) were obtained from Dr. B. R. G. Williams (the Cleveland Clinic Foundation) and were grown in α-MEM containing fetal bovine serum and antibiotics as previously described (Yang, Y. L. et al. EMBO J. 14:6095-6106 (1995); Der, S. D. et al., Proc. Natl. Acad. Sci. USA 94:3279-3283 (1997)).

The Dearing strain of reovirus serotype 3 used in these studies was propagated in suspension cultures of L cells and purified according to Smith (Smith, R. E. et al., (1969) Virology, 39:791-800) with the exception that β-mercaptoethanol (β-ME) was omitted from the extraction buffer. Reovirus labeled with [$^{35}$S]methionine was grown and purified as described by McRae and Joklik (McRae, M. A. and Joklik, W. K., (1978) Virology, 89:578-593). The particle/PFU ratio for purified reovirus was typically 100/1.

Immunofluorescent Analysis of Reovirus Infection

For the immunofluorescent studies the NIH-3T3, TNIH#5, H-ras, EJ-ras, 2H1 (+/−$ZnSO_4$), and THC-11 cells were grown on coverslips, and infected with reovirus at a multiplicity of infection (MOI) of ~10 PFU cell or mock-infected by application of the carrier agent (phosphate-buffered saline, PBS) to the cells in an identical fashion as the administration of virus to the cells. At 48 hours postinfection, cells were fixed in an ethanol/acetic acid (20/1) mixture for 5 minutes, then rehydrated by sequential washes in 75%, 50% and 25% ethanol, followed by four washes with phosphate-buffered saline (PBS). The fixed and rehydrated cells were then exposed to the primary antibody (rabbit polyclonal anti-reovirus type 3 serum diluted 1/100 in PBS) [antiserum prepared by injection of rabbits with reovirus serotype 3 in Freund's complete adjuvant, and subsequent bleedings] for 2 hours at room temperature. Following three washes with PBS, the cells were exposed to the secondary antibody [goat anti-rabbit IgG (whole molecule)-fluorescein isothiocyanate conjugate (FITC) [Sigma ImmunoChemicals F0382] diluted 1/100 in PBS containing 10% goat serum and 0.005% Evan's Blue] for 1 hour at room temperature. Finally, the fixed and treated cells were washed three more times with PBS and then once with double-distilled water, dried and mounted on slides in 90% glycerol containing 0.1% phenylenediamine, and viewed with a Zeiss Axiophot microscope on which Carl Zeiss camera was mounted (the magnification for all pictures was 200×).

Detection of MAP Kinase (ERK) Activity

The PhosphoPlus p44/42 MAP kinase (Thr202/Tyr204) Antibody kit (New England Biolabs) was used for the detection of MAP kinase in cell lysates according to the manufacturer's instructions. Briefly, subconfluent monolayer cultures were lysed with the recommended SDS-containing sample buffer, and subjected to SDS-PAGE, followed by electroblotting onto nitrocellulose paper. The membrane was then probed with the primary antibody (anti-total MAPK or is anti-phospho-MAPK), followed by the horseradish peroxidase (HRP)-conjugated secondary antibody as described in the manufacturer's instruction manual.

Radiolabelling of Reovirus-Infected Cells and Preparation of Lysates

Confluent monolayers of NIH-3T3, TNIH#5, H-ras, EJ-ras, 2H1 (+/−$ZnSO_4$), and THC-11 cells were infected with reovirus (MOI ~10 PFU/cell). At 12 hours postinfection, the media was replaced with methionine-free DMEM containing 10% dialyzed FBS and 0.1 mCi/ml [$^{35}$S]methionine. After further incubation for 36 hours at 37° C., the cells were washed in phosphate-buffered saline (PBS) and lysed in the same buffer containing 1% Triton X-100, 0.5% sodium deoxycholate and 1 mM EDTA. The nuclei were then removed by low speed centrifugation and the supernatants were stored at −70° C. until use.

Preparation of Cytoplasmic Extracts for In Vitro Kinase Assays

Confluent monolayers of the various cell lines were grown on 96 well cell culture plates. At the appropriate time postinfection the media was aspirated off and the cells were lysed with a buffer containing 20 mM HEPES [pH 7.4], 120 mM KCl, 5 mM $MgCl_2$, 1 mM dithiothrietol, 0.5% Nonidet P-40, 2 μg/ml leupeptin, and 50μg/ml aprotinin. The nuclei were then removed by low-speed centrifugation and the supernatants were stored at −70° C. until use.

Cytoplasmic extracts were normalized for protein concentrations before use by the Bio-Rad protein microassay method. Each in vitro kinase reaction contained 20 μl of cell extract, 7.5 μl of reaction buffer (20 mM HEPES [pH 7.4], 120 mM KCl, 5 mM $MgCl_2$, 1 mM dithiothrietol, and 10% glycerol) and 7.0 μl of ATP mixture (1.0 μCi[γ-$^{32}$P]ATP in 7

μl of reaction buffer), and was incubated for 30 minutes at 37° C. (Mundschau, L. J., and Faller, D. V., *J. Biol. Chem.*, 267: 23092-23098 (1992)). Immediately after incubation the labeled extracts were either boiled in Laemmli SDS-sample buffer or were either precipitated with agarose-poly(I) poly (C) beads or immunoprecipitated with an anti-PKR antibody.

Agarose Poly(I)Poly(C) Precipitation

To each in vitro kinase reaction mixture, 30 μl of a 50% Ag poly(I) poly(C) Type 6 slurry (Pharmacia LKB Biotechnology) was added, and the mixture was incubated at 4° C. for 1 h. The Ag poly(I) poly(C) beads with the absorbed, labeled proteins were then washed four times with wash buffer (20 mM HEPES [7.5 pH], 90 mM KCl, 0.1 mM EDTA, 2 mM dithiothrietol, 10% glycerol) at room temperature and mixed with 2× Laemmli SDS sample buffer. The beads were then boiled for 5 min, and the released proteins were analyzed by SDS-PAGE.

Polymerase Chain Reaction

Cells at various times postinfection were harvested and resuspended in ice cold TNE (10 mM Tris [pH 7.8], 150 mM NaCl, 1 mM EDTA) to which NP-40 was then added to a final concentration of 1%. After 5 minutes, the nuclei were pelleted and RNA was extracted from the supernatant using the phenol:chloroform procedure. Equal amounts of total cellular RNA from each sample were then subjected to RT-PCR (Wong, H., et al., (1994) *Anal. Biochem.*, 223:251-258) using random hexanucleotide primers (Pharmacia) and RTase (GIBCO-BRL) according to the manufacturers' protocol. The cDNA's from the RT-PCR step was then subjected to selective amplification of reovirus s1 cDNA using suitable primer sequences derived from the S1 sequence determined previously (Nagata, L., et al., (1984) *Nucleic Acids Res.*, 12:8699-8710). GAPDH primers (Wong, H., et al., (1994) *Anal. Biochem.*, 223:251-258) were used to amplify a predicted 306 bp GAPDH fragment which served as a PCR and gel loading control. Selective amplification of the s1 and GAPDH cDNA's was performed using Taq DNA polymerase (GIBCO-BRL) according to the manufacturers' protocol using a Perkin Elmer Gene Amp PCR system 9600. PCR was carried out for 28 cycles with each consisting of a denaturing step for 30 seconds at 97° C., annealing step for 45 seconds at 55° C., and polymerization step for 60 seconds at 72° C. PCR products were analyzed by electrophoresis through an ethidium bromide-impregnated TAE-2% agarose gel and photographed under ultra-violet illumination with Polaroid 57 film.

Immunoprecipitation and SDS-PAGE Analysis

Immunoprecipitation of $^{35}$S-labeled reovirus-infected cell lysates with anti-reovirus serotype 3 serum was carried out as previously described (Lee, P. W. K. et al. (1981) *Virology*, 108:134-146). Immunoprecipitation of $^{32}$P-labeled cell lysates with an anti-PKR antibody (from Dr. Michael Mathews, Cold Spring Harbor) was similarly carried out. Immunoprecipitates were analyzed by discontinuous SDS-PAGE according to the protocol of Laemmli (Laemmli, U. K., (1970) *Nature*, 227:680-685).

Example 1

Effect of Prior Reovirus Exposure on Survivability

C3H mice were challenged with an injection of reovirus as described above. After two weeks, antibodies to reovirus were detected in these animals. Animals exposed to reovirus and animals with no prior exposure were given a C3 tumor allograft. Following tumor establishment, live or UV-inactivated reovirus was administered to all animals. Animals with previous exposure to reovirus had lower incidence of complete tumor regression than did mice with no prior exposure. Three of nine (33%) challenged animals had complete tumor regression versus six of nine (66%) of mice with no prior exposure to reovirus.

Example 2

Co-Administration of Reovirus with an Immune Suppressive Agent to Decrease the Effective Dose It has been demonstrated that reovirus can act as an oncolytic agent in both immune deficient and immune competent animals, although immune competent animals require increased dosage of virus and increased frequency of treatment. To demonstrate that co-administration of reovirus in the presence of an immune suppressive agent allows for a decreased dosage and frequency of treatment in immune competent animals, C3H mice will be implanted with tumors derived from ras-transformed C3H 10T1/2 cells. Animals will then be treated either with an immune suppressive agent prior to the start of or at the time of treatment or mock-treated. Animals in these two groups will be treated either with a single intratumoral injection of reovirus or mock treated with UV-inactivated reovirus. In a second and third trial animals, will be treated or mock-treated with either 3 or 5 injections of reovirus on alternating days. Animals are followed for tumor regression for a 4 week period and sacrificed at the end of the fourth week. Results will show that treatment with an immune suppressive agent in addition to reovirus results in more effective tumor regression than treatment with reovirus alone. Animals treated with an immune suppressive agent will be found to require lower numbers and fewer administrations of reovirus to effect lysis.

Example 3

Co-Administration of Reovirus with an Immune Suppressive Agent to Augment Remote Tumor Regression It has been demonstrated that a single injection of reovirus is capable of causing tumor regression when delivered systemically in immune deficient mice. It has also been demonstrated that systemic delivery of reovirus is capable of causing tumor regression in immune competent animals, although increased dosages and frequency of treatment were required to elicit equivalent results to what were observed in immune deficient animals. To demonstrate that the use of an immune suppressive agent can alleviate the requirement for higher doses in these immune competent animals, C3H mice are implanted with tumors derived from ras-transformed C3H 10T1/2 cells on sites overlying their hind flanks. Animals are then either treated with an immune suppressive agent or are mock-treated. These two groups are then either treated with single intravenous injection of reovirus or are treated with UV-inactivated reovirus. In a second and third trial, animals are administered 3 or 5 intravenous reovirus or UV-inactivated reovirus injections every second day. Animals are followed for a 4 week period measuring tumor regression every second day. All animals are sacrificed at the end of week four. Results will show that treatment with an immune suppressive agent in addition to reovirus results in more effective tumor regression than treatment with reovirus alone. Animals treated with an immune suppressive agent will be found to require lower numbers and fewer administrations of reovirus to effect lysis.

Example 4

Extracorporeal Immunoadsorption

In order to prevent the host immune system from removing the therapeutically applied reovirus, selective removal of the immune constituents, such as B cells, T cells and antibodies, that may interfere with the systemic delivery is effected prior to the therapeutic delivery of reovirus.

Removal of either or both B cell and T cell populations can be conducted through blood filtration coupled with extracorporeal compounds that can remove the cell populations, for example, immobilized antibodies that recognize specific receptors of the cell population being removed.

Selective removal of antibodies can also prevent the host's immune system from removing the therapeutic virus. Preventing antibody interaction with the virus can also assist systemic therapeutic treatment of reovirus. This can be accomplished by several methods:

1) removal of anti-reovirus antibodies by heme-dialysis and passing the blood over immobilized reovirus (selective antibody removal);

2) removal of all IgG antibodies by heme-dialysis and passing the blood over immobilized protein A, such as PROSORBA™ (Cypress Bioscience, San Diego, Calif.)

3) administration of humanized anti-idiotypic antibody, where the idiotype is against reovirus.

Procedures for extracorporeal immunoadsorption are described in U.S. Pat. No. 4,711,839 to Singhal and U.S. Pat. No. 4,681,870 to Balint et al., which are incorporated herein by reference in their entirety.

It is understood that in the methods of this invention, reovirus is administered, immune constituents are removed, and reovirus may be administered to the patient again. These steps may be repeated as necessary. The number of times this method is repeated may be determined by a skilled medical practitioner based upon the condition of the patient.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of treating a ras-mediated proliferative disorder comprising neoplastic cells in a mammal, comprising the steps of:

a) administering to the neoplastic cells in said mammal an effective amount of an immune suppressive agent; and b) administering to the neoplastic cells in said mammal an effective amount of one or more mammalian reoviruses, wherein the immune suppressive agent is administered prior to administration of the mammalian reovirus.

2. The method of claim 1, wherein the mammalian reovirus is administered under conditions which result in substantial lysis of the neoplastic cells.

3. The method of claim 1, wherein one dose of immune suppressive agent is administered to the mammal.

4. The method of claim 1, wherein one, three or five doses of the mammalian reovirus is administered to the mammal.

5. The method of claim 3, wherein one, three or five doses of the mammalian reovirus is administered to the mammal.

6. The method of claim 1, wherein the reovirus is a human reovirus.

7. The method of claim 1, wherein the mammalian reovirus is selected from the group consisting of serotype 1 reovirus, serotype 2 reovirus and serotype 3 reovirus.

8. The method of claim 1, wherein the mammalian reovirus is serotype 3 reovirus.

9. The method of claim 1, wherein the mammalian reovirus is immunoprotected.

10. The method of claim 1, wherein the mammalian reovirus is a recombinant reovirus.

11. The method of claim 1, wherein the ras-mediated proliferative disorder is a neoplasm.

12. The method of claim 11, wherein the neoplasm is a solid neoplasm.

13. The method of claim 11, wherein the neoplasm is selected from the group consisting of lung cancer, prostate cancer, colorectal cancer, thyroid cancer, renal cancer, adrenal cancer, liver cancer, pancreatic cancer, breast cancer and central and peripheral nervous system cancer.

14. The method of claim 11, wherein the neoplasm is a hematopoietic neoplasm.

15. The method of claim 5, wherein the mammalian reovirus is administered by injection into or near the solid neoplasm.

16. The method of claim 1, wherein the mammalian reovirus is administered intravenously or intraperitoneally into the mammal.

17. The method of claim 1, wherein the mammal is a human.

18. The method of claim 1, wherein approximately 1 to $10^{15}$ plaque forming units of mammalian reovirus/kg body weight are administered.

19. The method of claim 1, wherein the immune suppressive agent is selected from the group consisting of radiation therapy, cyclic steroids, cyclosporin, rapamycin, tacrolimus, mycophenolic acid, azathioprine, and anti-anti-reovirus antibodies.

* * * * *

UNITED STATES PATENT AND TRADEMARK OFFICE
CERTIFICATE OF CORRECTION

| | |
|---|---|
| PATENT NO. | : 7,708,987 B2 |
| APPLICATION NO. | : 11/809195 |
| DATED | : May 4, 2010 |
| INVENTOR(S) | : Matthew C. Coffey |

Page 1 of 1

It is certified that error appears in the above-identified patent and that said Letters Patent is hereby corrected as shown below:

Column 1, line 4, please insert

--CROSS-REFERENCE TO RELATED APPLICATIONS

This application is a continuation of application No. 11/255,849, filed on Oct. 21, 2005, now Pat. No. 7,452,723, which is a continuation of application No. 10/401,032, filed on Mar. 28, 2003, now Pat. No. 7,014,847, which is a continuation of application No. 09/636,597, filed on Aug. 10, 2000, now Pat. No. 6,565,831, which is a continuation-in-part of application No. 09/256,824, filed on Feb. 24, 1999, now Pat. No. 6,136,307, which is a continuation-in-part of application No. 08/911,383, filed on Aug. 13, 1997, now Pat. No. 6,110,461. The entire disclosure of each of the prior applications is hereby incorporated by reference--.

Signed and Sealed this

Tenth Day of August, 2010

David J. Kappos
*Director of the United States Patent and Trademark Office*